United States Patent [19]

Mohseni et al.

[11] Patent Number: 5,431,906
[45] Date of Patent: Jul. 11, 1995

[54] SOLID SHAVING COMPOSITIONS

[75] Inventors: Zia Mohseni; Robert E. Saute, both of Los Angeles, Calif.

[73] Assignees: Joseph Briana, San Gabriel; Thomas Briana, Altadena, both of Calif.

[21] Appl. No.: 180,254

[22] Filed: Jan. 12, 1994

[51] Int. Cl.⁶ .................................. A61K 7/15
[52] U.S. Cl. .................... 424/73; 424/70.1; 424/DIG. 5
[58] Field of Search ................ 424/73, DIG. 5

[56] References Cited

U.S. PATENT DOCUMENTS 4,381,293  4/1983  Michel ..................... 424/14
4,999,183  3/1991  Mackles et al. ........... 424/47

Primary Examiner—Thurman K. Page
Assistant Examiner—James M. Spear
Attorney, Agent, or Firm—Robbins, Berliner & Carson

[57] ABSTRACT

Solid shaving compositions comprising a soap base, a humectant (such as glycerin), water, a high molecular weight polyethylene oxide, and a suitable preservative or antioxidant. In preferred formulations, at least one anticorrosion agent is included as part of the composition. If desired, at least one silicone fluid additive, emulsifying agents, fragrances and/or colorants suitable for use in cosmetics or toiletries may also be added. The novel compositions are solids which may be produced in stick form and applied directly to the skin. The solid shaving compositions of the invention provide a desirable balance of properties, making them ideal for use as shaving aids.

18 Claims, No Drawings

SOLID SHAVING COMPOSITIONS

BACKGROUND OF THE INVENTION

This invention relates to the field of compositions for use as shaving assistants to soften hair and lubricate the skin when shaving with blades or razors.

Presently, the most commonly-available form of shaving preparation has been a foam-type shaving assistant, commonly referred to as shaving cream. Generally, such creams are provided in the form of dispensers (e.g., cans) containing a propellant gas and a composition which generates a foam or lather. As it is not practical to produce such dispensers for small amounts of shaving cream, these cans usually are of substantial size. As a consequence, the cans are not particularly convenient for use when travelling. In addition, the use of many conventional propellants (such as hydrocarbons and, in particular, chlorofluorocarbons) is contraindicated for economic and environmental reasons. Therefore, it would be desirable to provide an alternative form of composition for use in developing a suitable lather for shaving purposes.

U.S. Pat. No. 2,366,759 to Thomas et al. describes a brushless shaving preparation which may be prepared in a substantially anhydrous condition. The disclosed compositions comprise a mixture of vegetable oil (e.g., sesame, groundnut or olive) and a waxy ingredient (e.g., spermaceti or ozokerite). An emulsifying agent may be added to impart hydrophilic properties to the preparation.

U.S. Pat. No. 2,143,060 to Dzialoschinsky et al. describes a solid shaving preparation which evolves oxygen, comprising an intimate mixture of a staple oxygen-producing substance, a binder and a water-soluble filler to facilitate access of water to the oxygen-producing substance. A typical preparation comprises magnesium peroxide, gum arabic, sugar of milk, magnesium carbonate and hydrogen peroxide carbamide.

U.S. Pat. No. 2,838,442 to McMaster describes a shaving stick block comprising carboxymethyl cellulose, an alkali metal salt of an alkyl substituted aromatic sulfonic acid and an inorganic binding agent, such as colloidal magnesium aluminum silicate, formulated in combination with talc and a suitable pigment so as to permit easy application to the beard of the user.

U.S. Pat. No. 2,876,161 to Gieschi describes a brushless shave composition in solid stick form which comprises an oil-in-water solid gel. The non-oily acidic aqueous phase includes a normal chain fatty acid having at least 12 carbon atoms in the hydrocarbon chain and which is solid at room temperatures, as well as triethanolamine and a liquid, non-toxic lower alkylene glycol having from 3 to 6 carbon atoms. The oil phase comprises a mineral oil and lanolin.

U.S. Pat. No. 4,381,293 to Michel describes a shaving composition which is solid in form. This composition comprises a water-soluble polyethylene polymer having a molecular weight of 400,000 or less; a suitable tracking agent component, which may be formed by combining a pigment with a fatty acid-based molecule; a preservative component having bacteriocidal and fungicidal activity; a lubricant component, such as magnesium or zinc stearate; and an anti-caking component, such as silica gel.

In spite of the various suggestions provided in the prior art, such as the patents discussed above, there remains a need for a solid shaving aid composition which provides the desired balance of properties necessary for widespread acceptance by consumers.

SUMMARY OF THE INVENTION

In accordance with the present invention, there are provided solid shaving compositions comprising a soap base, a humectant (such as glycerin), water, a high molecular weight polyethylene oxide, and a suitable preservative or antioxidant. In many formulations, the addition of at least one anticorrosion agent provides significant advantages. In some formulations, it is further useful to include at least one silicone fluid additive and/or emulsifying agents as part of the composition. If desired, fragrances and/or colorants suitable for use in cosmetics or toiletries may also be added. The novel compositions are solids which may be produced in stick form and applied directly to the skin. The solid shaving compositions of the invention provide a desirable balance of properties, making them ideal for use as shaving aids.

DETAILED DESCRIPTION OF THE INVENTION

The solid shave compositions of the present invention are based on a solid carrier comprising a mixture of a solid soap composition with a humectant (typically, glycerin) and water. A variety of solid soap bases as are well known in the art may be employed, such as sodium and/or potassium cocoate, stearate, palmitate, myristate and mixtures thereof. A particularly preferred soap mixture is an 80/20 tallow/coconut sodium soap base. In addition to providing a solid base for the shaving composition, the soap serves as the main deodorizing component of the composition and imparts some antimicrobial activity to the composition as well. In addition, the soap absorbs wetness or perspiration in conjunction with the glycerin.

The humectant component, in addition to its properties as a skin moisturizing agent, generally acts in the inventive compositions as a plasticizer. While glycerin is the preferred humectant, suitable alternatives for all or a part of the humectant component include propylene glycol, sorbitol, hydrogenated corn syrup, sodium pyrrolidone carboxylate and mixtures thereof. A suitable glycerin for use in accordance with the present invention has a specific gravity at 25° C. of about 1.25 and comprises at least 95% by weight of glycerin. In addition, the starting material must meet all other quality standards (e.g., heavy metals and chlorinated compounds content, flavor, color, pH, redox, etc.) appropriate for its use in a cosmetics preparation. One suitable glycerin composition is available from Lonza, Inc., Williamsport, Pa. under the designation Star Glycerine, U.S.P.

The compositions of the invention generally comprise about 5% to about 50% by weight, preferably about 15% to about 30% by weight, of soap; about 10% to about 60% by weight, preferably about 30% to about 40% by weight, of humectant; and about 10% to about 50% by weight, preferably about 33% to about 37.5% by weight, of water.

The compositions of the invention typically further comprise a suitable preservative or antioxidant to prevent product degradation. In some compositions, a suitable preservative is propylparaben, $C_{10}H_{12}O_3$. As propylparaben hydrolyses rapidly at pH 10 and has limited preservative action above pH 8, a suitable alternative for some uses is o-phenylphenol (e.g., Dowicide A), which does not hydrolyze and which further acts as an antioxidant. Another useful antioxidant is tocopherol. A preferred antioxidant additive is Tenox-6, which is a composition comprising butyl hydroxytoluene (BHT), butyl hydroxyanisole (BHA) and propylgallate in a solvent and is available from Tennessee Eastman Co., Kingsport, Tenn. Generally, the antioxidant or preservative is present in an amount of about 0.05% to about 1.0% preferably about 0.1% to about 0.3% by weight.

In preferred embodiments of the inventive compositions, at least one silicone fluid is added to minimize tackiness and soapiness of the composition. The silicone additive also serves to improve the lubricity and spreading properties upon application of the composition to the skin. When included in the composition, the silicone additive is generally present in an amount of about 0.1% to about 5% by weight, preferably about 0.1 to about 0.2% by weight. An exemplary silicone additive is hexamethyl disiloxane, available from Dow Corning, Midland, Mich. under the designation Silicone D.C. 200. Other suitable silicone additives include dimethyl silicone and dimethyl siloxane-glycol copolymers.

In addition to the above ingredients, the inventive compositions comprise about 0.1% to about 20% by weight, preferably about 0.5% to about 6.0% by weight, of a high molecular weight polyethylene oxide (i.e., a polyethylene oxide having a molecular weight of at least about 1,000,000). This component serves as a thickener for the composition. Further, the addition of the high molecular weight polyethylene oxide permits a slip-on application of the composition to the skin, leaving a thin film of the composition thereon. The high molecular weight polyethylene oxide also serves as a lubrication agent. A particularly suitable high molecular weight polyethylene oxide is available from Union Carbide, New York, N.Y. under the designation POLYOX WSR N-12K. Other polyethylene oxide compositions having an approximate molecular weight of about 1,000,000 or greater would also be suitable for use in the inventive compositions.

In the aforementioned U.S. Pat. No. 4,381,293 to Michel, the incorporation into shaving compositions of polyethylene polymers of a molecular weight of 400,000 or less is described. In their product literature, Union Carbide and other distributors also recommend the use of polyethylene glycols to promote smoothness and lubricity. It is well known, however, that polyethylene glycols lose their effectiveness in the presence of soaps. Therefore, as a practical matter it is generally necessary (contrary to the teachings of Michel) to employ materials having a molecular weight in the range of at least about 1,000,000.

Unfortunately, polyethylene glycols even in this higher molecular weight range have appeared to deteriorate and to lose effectiveness as viscosifiers in a few days in the presence of soaps. As a consequence, they have not been generally recommended by the distributors for use in compositions such as described herein, which comprise in substantial part a soap base.

In the context of the inventive compositions, it did not appear reasonable that hydrolysis of the ether groups would occur when the pH of the compositions was no greater than about 10. Therefore, in order to determine the nature of the problem identified in the prior art, samples of the product were placed in a closed vessel connected to a water manometer. After a week, a gaseous volume loss was indeed apparent, due apparently to oxygen absorption. The addition of antioxidant at a level of 0.1% reduced this loss as follows:

p-monomethyl phenol—5% of loss;
butyl hydroxytoluene—8% of loss; and
butyl hydroxyanisole—10% of loss.

The use of Tenox-6, at a level of 0.2%, together with airtight packaging of the product after manufacture, resulted in a formulation exhibiting the dramatic lubricity and rheological properties of the high molecular weight polyglycols in a stabilized form. Therefore, in accordance with the present invention at least one antioxidant at a concentration of at least about 0.05%, and preferably at least about 0.1%, is employed in the formulation of preferred embodiments.

A vital factor in satisfactory shaving is the relative sharpness of the blade. In particular, it has been determined in connection with the development of the inventive compositions that a rapid deterioration of the blade edge occurs during shaving on skin with acid and/or salt content sufficiently high to overcome the buffering ability of the soap. In general, the departure of metal ions from a cornered surface proceeds at a rate proportional to the sharpness of the corner. Therefore, it is reasonable to expect that a serious problem is presented with the sharp-edged blades typically used in shaving.

In order to study the rate of departure of ferrous ions from a blade edge, a steel razor blade was stropped to remove surface coatings and the edge immersed in a 5% solution of the shaving composition. A calomel electrode was also immersed in the composition, and the two connected by a high impedance voltmeter with a 5 megohm resistance in parallel to permit a stable rate of electrolysis. The migration of positively-charged ferrous ions from the blade was found to result in the development of a negative charge thereon. With a typical formulation comprising the ingredients discussed above, a value of $-350$ mv was obtained in the above test.

In view of this migration, it has been found desirable in accordance with preferred embodiments of the present invention to incorporate at least one corrosion inhibitor into the composition. This inhibitor should be harmless to the skin and adherent to the edge of the blade. In accordance with the present invention, the preferred formulations therefore comprise as corrosion inhibitors at least one quaternary ammonium salt. In the test described above, upon addition of 3% quaternary salt as corrosion inhibitor to the test formulation the magnitude of migration was reduced, as indicated by a measured value of only $-75$ mv.

A further advantageous feature of the quaternary salts preferred for use as anticorrosion agents is that they are also generally effective as conditioning agents. These salts are generally surface-active, and thus help to condition the film and to maintain the film on the skin. In addition, the salts may have some antimicrobial properties as well. In general, quaternary ammonium salts which form insoluble precipitates with soaps and which have affinity for negatively charged metal surfaces are useful as anticorrosion agents. One suitable example is benzyl dimethyl stearylammonium chloride (stearalkonium chloride), as is available under the designation Carsoquat SDQ-85 from Lonza Inc., Williamsport, Pa. Other suitable quaternary salts include cetyl dimethyl benzyl ammonium chloride, cetyl dimethyl benzyl ammonium bromide and cetylpyridinium chloride. It is preferred to use quaternary salts with a major chain of about 18 carbon atoms (such as, e.g., stearyl), rather than shorter chain compounds of, e.g., about 12 carbons (such as lauryl). The corrosion inhibitors/conditioning agents comprise about 1% to about 5% by weight, preferably about 2% to about 3% by weight, of preferred embodiments of the composition.

In some formulations, it is useful to include emulsifying and/or conditioning agents as part of the composition. The emulsifying agent acts as an emulsion hardener, thereby serving to maintain the composition in solid form; the emulsifying agent also serves as a stabilizer. As an emulsifying agent, glyceryl stearate is particularly useful. A suitable form is available from Glyco, Greenwich, Conn. under the designation Aldo MS FG. Alternatively, ammonium isostearate and glyceryl ricinoleate are also suitable for use as emulsifying agents. When present, the emulsifying agents comprise up to about 5% by weight, preferably up to about 2% by weight, of the composition.

Finally, it is often desirable to add one or more colorant and/or fragrance components to the compositions to make them more desirable to the consumer. In this regard, any number of a wide variety of different colorants and fragrances well known in the industry as suitable for use in cosmetics or toiletries may be employed in amounts effective to achieve the desired result. One suitable colorant is B-3282 Cosmetic Brown, available from Kohnstamm, New York, N.Y. Suitable fragrances include Fragrance OSC Mod. A3289 available from Felton International, Brooklyn, N.Y. and JN 33033 available from Belmay West, Van Nuys, Calif.

The compositions of the present invention may be prepared in the following manner. As a first step, a suitable soap base (e.g., an 80/20 tallow/coconut sodium soap base) is prepared. The soap base is then heated to an elevated temperature (e.g., 70°-80° C.) and mixed with the glycerin. At this stage, anticorrosion and/or emulsifying agents may be added, if desired. The mixture is then removed from the heat and the polyethylene glycol is dusted into the mixture; in addition, certain antioxidants (e.g., Tenox-6) and/or colorants may be added at this stage, if convenient. After the mixture has been allowed to cool to about 60°-65° C., the silicone additive (if used), water and other antioxidant(s) (e.g., propylparaben) are added. If employed, the fragrance is added just before pouring at, e.g., 55° C.

The compositions of the present invention exhibit a number of significant advantages. The formulations of the composition are such that the product can readily be melted and poured into a suitable dispenser. The compositions spread smoothly on the skin. In particular with those embodiments containing a silicone component, there is nonetheless no significant generation of suds. In addition, the film does not dry prematurely on the skin during the shave. The humectant (e.g., glycerin) serves as an anti-irritant and skin moisturizer; moreover, the high humectant ratio aids in easy rinsing after use. The mucilaginous properties of the formula are maintained over a significant period of time by virtue of the antioxidant.

In ordinary shaving, when a blade pushes against a softened hair, the blade pushes the generally limp hair over and cuts it obliquely. To obtain a reasonably close shave, it is then necessary to cut the hair again from the opposite direction. While a fine grained lather, such as from an aerosol foam, may somewhat reduce the limpness of the hair, the shaving compositions heretofore available have not been entirely satisfactory.

Therefore, it is a particular objective of the present invention to provide a solution to the problem of obtaining a close shave without the need to resort to reverse shaving strokes. To this end, the hairs are encased in a firm gel so that cutting may be effected in a transverse manner, rather than longitudinally. The formulations of the present invention, especially by virtue of their high molecular weight polyethylene oxide content, have the desirable property of gelling up after being rubbed on the skin. This effect is advantageously reinforced, in accordance with a preferred aspect of the present invention, through the use of formulations which lose water from the solvent system in humidities lower than 80% R.H. This provides in practice the best ratio of "sweating" versus drying out of the formulation. After the beard is fully swollen by washing with water, the viscosity of the solid shave composition is such that water loss during the shaving process is substantially prevented. As a result, the hairs are cut easily in a single stroke.

Finally, formulations described herein in accordance with preferred embodiments of the invention provide the additional advantage that the sharpness of the blade used in shaving is maintained for a significantly longer period than is the case with comparable shaving compositions. This is a consequence of the inclusion in the preferred compositions of at least one quaternary ammonium salt as anticorrosion agent.

The invention will be better understood by reference to the following examples which are intended for purposes of illustration and are not to be construed as in any way limiting the scope of the present invention, which is defined in the claims appended hereto. Unless otherwise indicated, all percentages are by weight based on the weight of the entire composition.

EXAMPLE 1

The following composition provides a shaving aid composition in solid form with a desirable balance of properties.

| Water | 37.5 |
|---|---|
| Glycerin | 40.0 |
| Polyox WSR N-12K | 6.0 |
| Tenox-6 | 0.2 |
| Propylparaben | 0.1 |
| Soap 80/20 | 15.0 |
| Dow Corning 200 | 0.2 |
| Belmay JN 33033 | 1.0 |

After preparation of an 80/20 tallow/coconut sodium soap base, the soap base is heated and mixed with the glycerin component until the glycerin is completely dissolved. The mixture is removed from the heat, Tenox 6 is added and the Polyox WSR N-12K is dusted into the mixture. Once cooling has begun, to the mixture are added water, propylparaben and Dow Corning 200. Just before pouring at the lowest temperature at which the mixture is still liquid, Belmay JN 33033 is added.

EXAMPLE 2

An alternative formulation is prepared as follows.

| Water | 33.00 |
|---|---|
| Glycerin | 30.00 |
| Silicone D.C. 200 | 0.20 |
| Soap 80/20 | 30.00 |
| Polyox WSR N-12K | 0.50 |

| | |
|---|---|
| Carsoquat SDQ-85 | 3.00 |
| Aldo MS | 2.00 |
| Cosmetic Brown | 0.01 |
| Propylparaben | 0.10 |
| Tenox-6 | 0.20 |
| Fragrance OSC Mod. A3289 | 0.25 |

As in Example 1, an 80/20 tallow/coconut sodium soap base is prepared. In this case, however, the glycerin is added and the mixture is heated to 75° C. with continued mixing until the glycerin is completely dissolved. The Carsoquat SDQ-85 and Aldo MS are then added, and the resultant mixture removed from the heat. The Tenox-6 is added; the Polyox WSR N-12K and Cosmetic Brown are dusted into the mixture. Cooling is begun at 65° C., with addition of water, propylparaben and Silicone D.C. 200. The fragrance is added just before pouring at 55° C.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. A solid shaving composition comprising:
   about 5% to about 50% by weight of a soap base;
   about 10% to about 60% by weight of a humectant;
   about 0.1% to about 20% by weight of a polyethylene oxide having a molecular weight of at least about 1,000,000;
   about 0.05% to about 1% by weight of at least one antioxidant;
   about 1% to about 5% by weight of at least one anticorrosion agent; and the balance by weight of water.

2. A solid shaving composition according to claim 1, comprising:
   about 15% to about 30% by weight of a soap base;
   about 30% to about 40% by weight of a humectant;
   about 0.5% to about 6% by weight of a high molecular weight polyethylene oxide;
   about 0.1% to about 0.3% by weight of at least one antioxidant; and
   the balance by weight of water.

3. A solid shaving composition comprising:
   about 5% to about 50% by weight of a soap base;
   about 10% to about 60% by weight of a humectant;
   about 0.1% to about 20% by weight of a high molecular weight polyethylene oxide having a molecular weight of at least about 1,000,000;
   about 0.05% to about 1% by weight of at least one antioxidant;
   about 0.1 to about 0.2% by weight of at least one silicone; and
   the balance by weight of water.

4. A solid shaving composition according to claim 1, wherein said anticorrosion agent is a quaternary ammonium salt.

5. A solid shaving composition according to claim 1, further comprising at least one silicone in an amount of about 0.1% to about 5% by weight of the composition.

6. A solid shaving composition according to claim 5, wherein said at least one silicone comprises about 0.1% to about 0.2% by weight of the composition.

7. A solid shaving composition according to claim 1, wherein said soap base is an 80/20 tallow/coconut sodium soap base.

8. A solid shaving composition according to claim 1, wherein said at least one antioxidant is selected from the group consisting of propylparaben, butyl hydroxytoluene, butyl hydroxyanisole, propylgallate, tocopherol, o-phenylphenol and mixtures thereof.

9. A solid shaving composition according to claim 1, wherein said at least one silicone is selected from the group consisting of dimethyl silicone, hexamethyl disiloxane and dimethyl siloxane-glycol copolymers.

10. A solid shaving composition comprising:
    about 5% to about 50% by weight of a soap base;
    about 10% to about 60% by weight of a humectant;
    about 0.1% to about 20% by weight of a high molecular weight polyethylene oxide having a molecular weight of at least about 1,000,000;
    about 0.05% to about 1% by weight of at least one antioxidant;
    up to about 2% by weight of at least one emulsifying agent; and
    the balance by weight of water.

11. A solid shaving composition according to claim 1, wherein said humectant is selected from the group consisting of glycerin, propylene glycol, sorbitol, hydrogenated corn syrup, sodium pyrrolidone carboxylate and mixtures thereof.

12. A solid shaving composition according to claim 11, wherein said humectant is glycerin.

13. A solid shaving composition according to claim 1, further comprising at least one emulsifying agent.

14. A solid shaving composition according to claim 13, wherein said at least one emulsifying agent is present in an amount of up to about 2% by weight of the composition.

15. A solid shaving composition according to claim 13, wherein said at least one emulsifying agent is selected from the group consisting of glyceryl stearate, ammonium isostearate, glyceryl ricinoleate and mixtures thereof.

16. A solid shaving composition according to claim 1, further comprising at least one additive selected from the group consisting of colorants and fragrances suitable for use in cosmetics or toiletries.

17. A solid shaving composition according to claim 1 comprising:
    about 30% by weight of a tallow/coconut sodium soap base;
    about 30% by weight glycerin:
    about 0.5% by weight of a high molecular weight polyethylene oxide;
    about 0.2% by weight of hexamethyl disiloxane;
    about 0.3% by weight of at least one antioxidant;
    about 3.0% by weight of at least one quaternary ammonium salt;
    about 2.0% by weight of stearyl alcohol; and
    the balance of about 33% by weight of water.

18. A solid shaving composition according to claim 3 comprising:
    about 15% by weight of a tallow/coconut sodium soap base;
    about 40% by weight glycerin:
    about 6.0% by weight of a high molecular weight polyethylene oxide;
    about 0.2% by weight of hexamethyl disiloxane;
    about 0.3% by weight of at least one antioxidant; and
    the balance of about 37.5% by weight of water.

* * * * *